(12) United States Patent
Kotecki et al.

(10) Patent No.: US 7,409,869 B1
(45) Date of Patent: Aug. 12, 2008

(54) RESISTANCE TEST METHOD

(75) Inventors: Damian J. Kotecki, Mentor, OH (US); Sudarsanam S. Babu, Knoxville, TN (US)

(73) Assignee: Lincol Global, Inc., City of Industry, CA (US)

( * ) Notice: Subject to any disclaimer, the term of this patent is extended or adjusted under 35 U.S.C. 154(b) by 53 days.

(21) Appl. No.: 11/131,685

(22) Filed: May 18, 2005

(51) Int. Cl.
- *G01N 3/10* (2006.01)
- *G01N 3/18* (2006.01)
- *G01N 3/36* (2006.01)

(52) U.S. Cl. .............. 73/797; 73/796; 73/810
(58) Field of Classification Search .............. 73/850, 73/789, 794, 796, 797, 810, 849, 851
See application file for complete search history.

(56) References Cited

U.S. PATENT DOCUMENTS

| | | | |
|---|---|---|---|
| 2,685,195 A * | 8/1954 | Streblow ............ | 374/47 |
| 3,100,253 A * | 8/1963 | O'Connor ............ | 219/503 |
| 3,665,751 A * | 5/1972 | Paine et al. ............ | 374/47 |
| 4,256,945 A * | 3/1981 | Carter et al. ............ | 219/229 |
| 4,523,475 A * | 6/1985 | Bills et al. ............ | 73/781 |
| 5,055,648 A * | 10/1991 | Iceland et al. ............ | 219/601 |
| 5,092,179 A | 3/1992 | Ferguson | |
| 5,195,378 A * | 3/1993 | Ferguson ............ | 73/790 |
| 5,202,542 A * | 4/1993 | Ferguson ............ | 219/50 |
| 5,242,510 A * | 9/1993 | Begin ............ | 148/321 |
| 5,315,085 A * | 5/1994 | Ferguson ............ | 219/50 |
| 6,232,000 B1 * | 5/2001 | Singh et al. ............ | 428/685 |

FOREIGN PATENT DOCUMENTS

DE     3603220 A1 *    8/1987

OTHER PUBLICATIONS

English Translation of DE 3603220. Translated Jul. 2007. Translated by FLS,. Inc.*

* cited by examiner

*Primary Examiner*—Edward Lefkowitz
*Assistant Examiner*—Punam Patel
(74) *Attorney, Agent, or Firm*—Fay Sharpe LLP

(57) ABSTRACT

A method for evaluating thermal fatigue resistance for a welding consumable alloy can include the following steps: placing a test specimen of a welding consumable alloy in a testing device such that a tensile load and a compressive load can be introduced to the test specimen; heating the test specimen to a first temperature; applying a compressive force to the test specimen while heating the test specimen; cooling the test specimen to a second temperature; and applying a tensile force to the test specimen while cooling the test specimen.

8 Claims, 7 Drawing Sheets

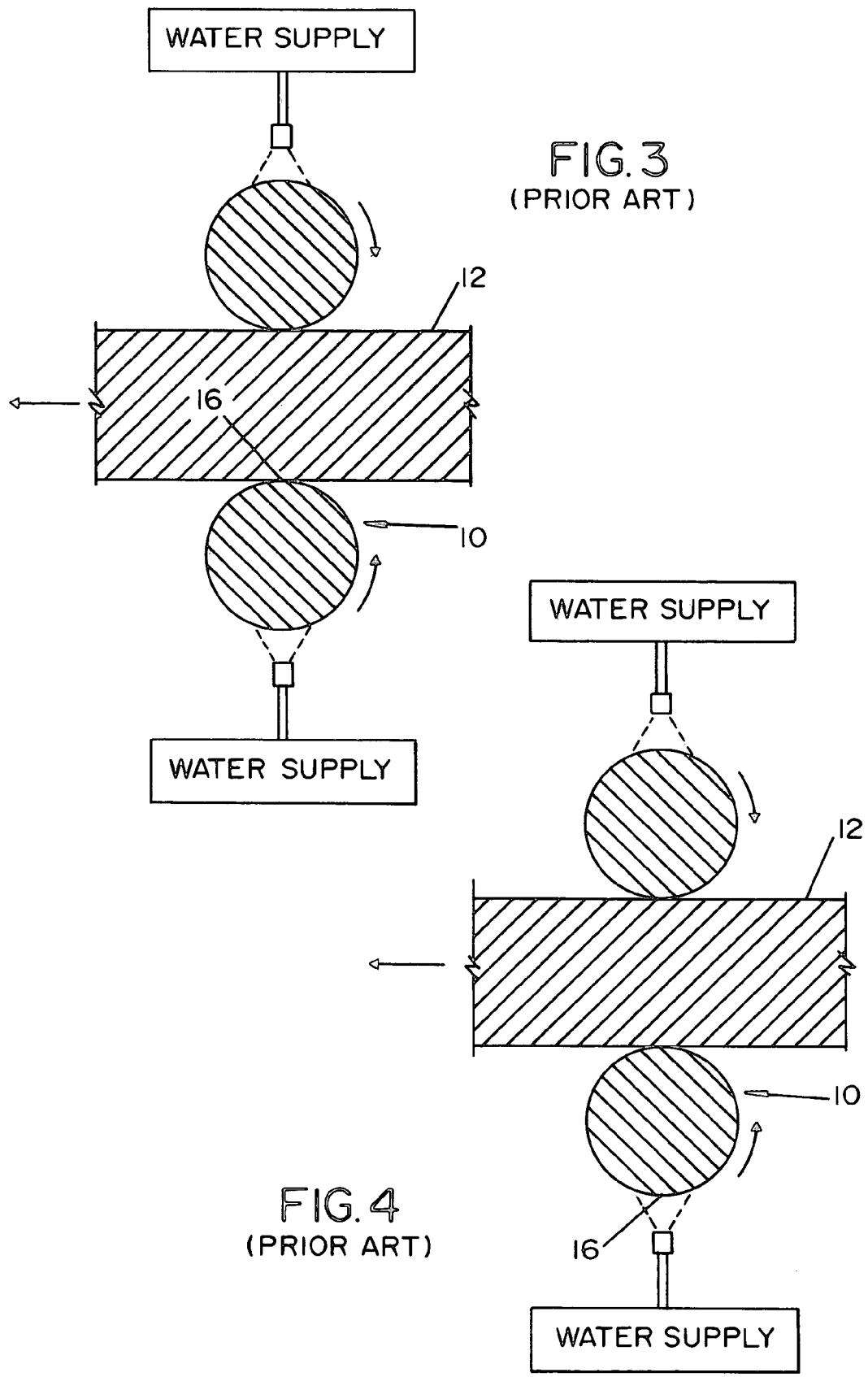

RESISTANCE TEST METHOD

BACKGROUND

With reference to FIG. 1, caster rolls 10 control and guide the progress of a billet or slab 12 of steel that is produced by a caster. Caster rolls wear because of corrosion, abrasion, plastic deformation and thermal fatigue and cracking. Repairing caster rolls can minimize the need for costly shutdowns and prevent expensive breakdowns.

The repairing or rebuilding of caster rolls involves depositing an alloy in the area of the caster roll that is being repaired. Typically, a tubular metal-cored wire is deposited on the caster roll via submerged arc welding. Layers of alloy can be deposited on the caster roll; the layers include a butter pass, buildup layer(s), and hardfacing layer(s). For ease of understanding the figures, the individual layers are not depicted in FIGS. 2, 3 and 4. After the caster roll has been hardfaced, the alloy that was deposited on the caster roll undergoes many stresses and strains when the caster roll is put back on line guiding hot steel.

As mentioned above, the caster roll 10 guides a hot billet or slab of steel 12. With reference to FIG. 2, for a hardfaced caster roll 10, alloy that has been deposited over the surface of the roll is heated along a line of contact 16 with the hot steel. With reference to FIG. 3, the heated hardfacing alloy along this line of contact 16 tries to expand in all directions, but it is confined by the roll body in all directions, except that it can expand up into the hot billet or slab of steel 12 when the alloy comes in contact with the steel. This expansion is possible because the steel is plastic while hot. The line of contact 16 does not expand in other directions because it is confined by the body of the caster roll. As the alloy along the line of contact 16 expands up into the hot steel, the alloy along the line of contact is under compression because of the mass of the remainder of the roll. As the caster roll 10 rotates, the alloy that was along the line of contact 16 no longer contacts the hot steel billet or slap 12. With reference to FIG. 4, the side of the caster roll 10 not in contact with the hot steel is typically sprayed with relatively cool water which also results in cooling of the hardfacing alloy and especially the alloy along the line of contact 16. The cooling of the alloy along the line of contact 16 results in the alloy contracting. This contraction causes tensile stresses. This cycle of compression while heating, followed by tension while cooling, is repeated along the line of contact 16 each time the roll rotates a full turn.

It is desirable to develop a test method to evaluate an alloy used to hardface caster rolls to determine the alloy's ability to withstand the thermal cycling discussed above.

SUMMARY OF THE INVENTION

A method for evaluating thermal fatigue resistance for a welding consumable alloy can include the following steps: placing a test specimen of a welding consumable alloy in a testing device such that a tensile load and a compressive load can be introduced to the test specimen; heating the test specimen to a first temperature; applying a compressive force to the test specimen while heating the test specimen; cooling the test specimen to a second temperature; and applying a tensile force to the test specimen while cooling the test specimen.

A method for evaluating thermal fatigue resistance for a welding consumable alloy can include the following steps: placing a test specimen in a testing device having opposing jaws, each end of the specimen being received by a respective jaw; heating the test specimen to a first temperature; moving at least one of the jaws toward the other jaw while heating the test specimen; cooling the test specimen to a second temperature; and moving at least one of the jaws away from the other jaw while cooling the test specimen.

A method for evaluating thermal fatigue resistance for a welding consumable alloy can include the following steps: placing a test specimen of a welding consumable alloy in a testing device such that a tensile strain and a compressive strain can be introduced to the test specimen; heating the test specimen to a first temperature; introducing a compressive strain to the test specimen while heating the test specimen; cooling the test specimen to a second temperature; and introducing a tensile strain to the test specimen while cooling the test specimen.

BRIEF DESCRIPTION OF THE DRAWINGS

FIG. 3 is a side elevation cross-sectional view of a hardfaced caster roll with a hot line of contact of the hardfacing alloy in contact with the slab or billet of steel.

FIG. 4 is a side elevation cross-sectional view of the same hardfaced caster roll of FIG. 3 after 180° of rotation with the formerly hot line of contact no longer in contact with the slab or billet of steel, but instead being cooled by the water spray.

DETAILED DESCRIPTION

The test method of this invented method for evaluating thermal fatigue resistance of an alloy, also known as "firecracking" resistance, generally involves heating a sample specimen 18 (FIG. 6) while the specimen is undergoing compressive strain and then cooling the specimen while the specimen is undergoing tensile strain. The load on the specimen is controlled to produce a small compressive strain during heating and a small tensile strain during cooling in each cycle of the test method. The sample specimen will typically be made of an alloy that will be used in a welding consumable, such as welding wire, and generally the more cycles that the test specimen can endure before fracture, the better the alloy.

Figure 6:
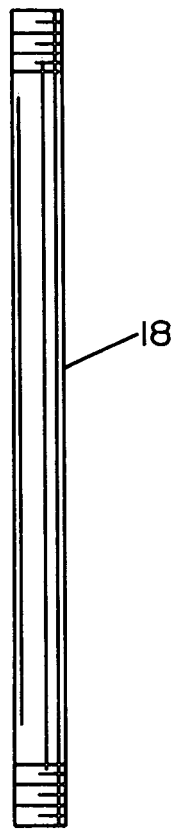
FIG. 6 is a side elevation view of a sample specimen for use in a method for evaluating thermal fatigue resistance of a welding consumable alloy.
Figure 7:
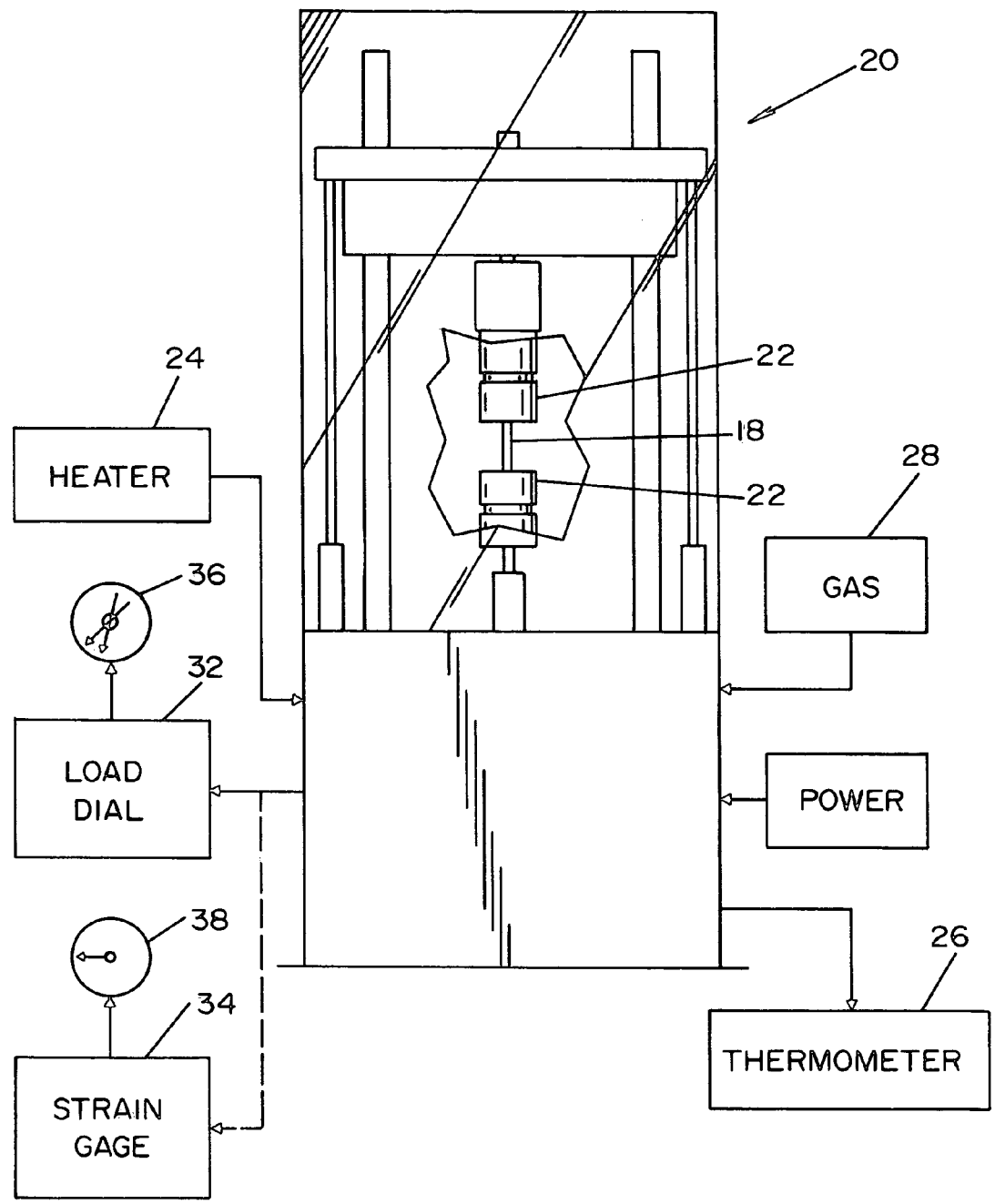
FIG. 7 is a schematic view of a thermal-mechanical testing system for use in a method for evaluating thermal fatigue resistance for a welding consumable alloy.

With reference to FIG. 6, the sample specimen 18 is shown specifically adapted for testing using thermal-mechanical testing system 20 (depicted schematically in FIG. 7) known as a Gleeble® 3500 available from Dynamic Systems, Inc. of Poestenkill, N.Y. The sample specimen is cylindrical having threaded ends. Other specimen designs may be used, for example with other thermal-mechanical testing systems capable of performing the following steps can also be used.

Generally, the sample specimen 18 is loaded into the testing machine 20 such that the specimen can be placed in both tension and compression. The depicted testing machine 20 includes jaws 22 that hold opposite threaded ends of the sample specimen. As is known in the art, at least one of the jaws is directed towards the other jaw to place the sample specimen in compression, and at least one of the jaws is directed away from the other jaw to place the sample specimen in tension. The testing machine 20 is also adapted to control the temperature of the test specimen. A heater 24 can be provided to control the temperature around the region of the test specimen. The heater 24 can be in electrical communication with the specimen 18 so that the specimen is heated via resistive heating. A thermocouple (not shown) can be attached to the sample specimen to measure its temperature via a thermometer 26. The heater 24 can be placed on a programmed temperature cycle where the resistance heating power that is supplied to the specimen is controlled to conform to a programmed temperature cycle. Argon gas can be introduced into the region around the sample specimen via a gas source 28. In the described method, the argon gas is introduced as the specimen is cooled. The use of argon gas can aid in avoiding oxidation of the sample specimen; however, other gases can also be used, including helium and air.

The thermo-mechanical testing system 20 also includes a load dial 32 and a strain gage 34, each of which are shown schematically. The load dial 32 displays the load being applied to the specimen 18 on a display 36, which is schematically depicted as an analog display but the display can also be digital. The strain gage 34 measures the change in length and/or diameter of the specimen and displays this information on a display 38, which is schematically depicted as an analog display but the display can also be digital. In the below-described method, the dilatation of the specimen is measured at the diameter of the specimen 18.

Figure 1:
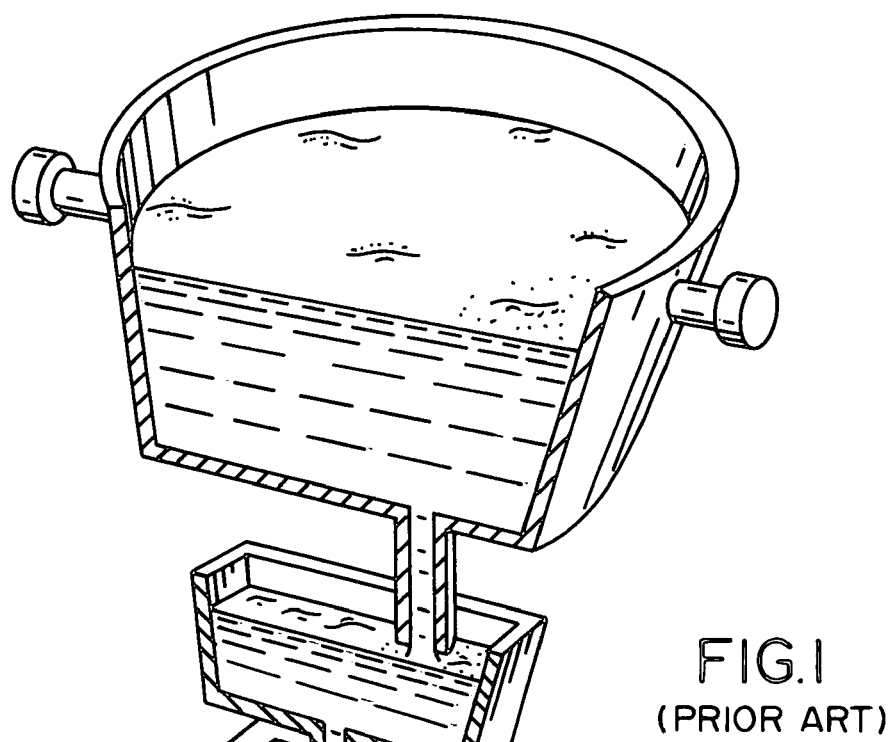
FIG. 1 is a perspective view of a portion of a known caster used to make a slab or billet of steel.
Figure 2:
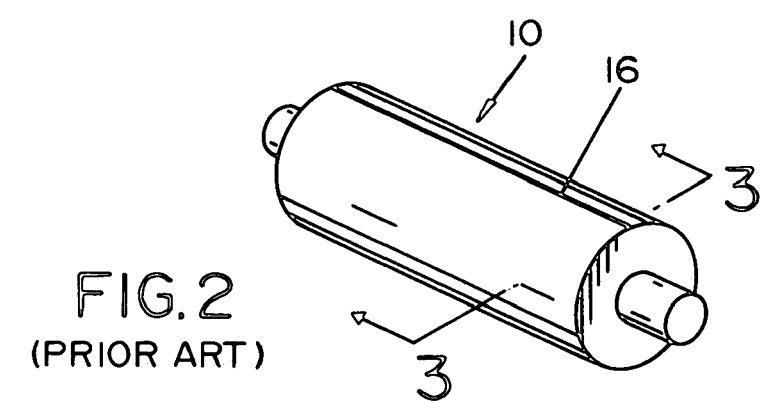
FIG. 2 is a perspective view of a caster roll illustrating a hot line of contact with a hot steel slab.
Figure 5:
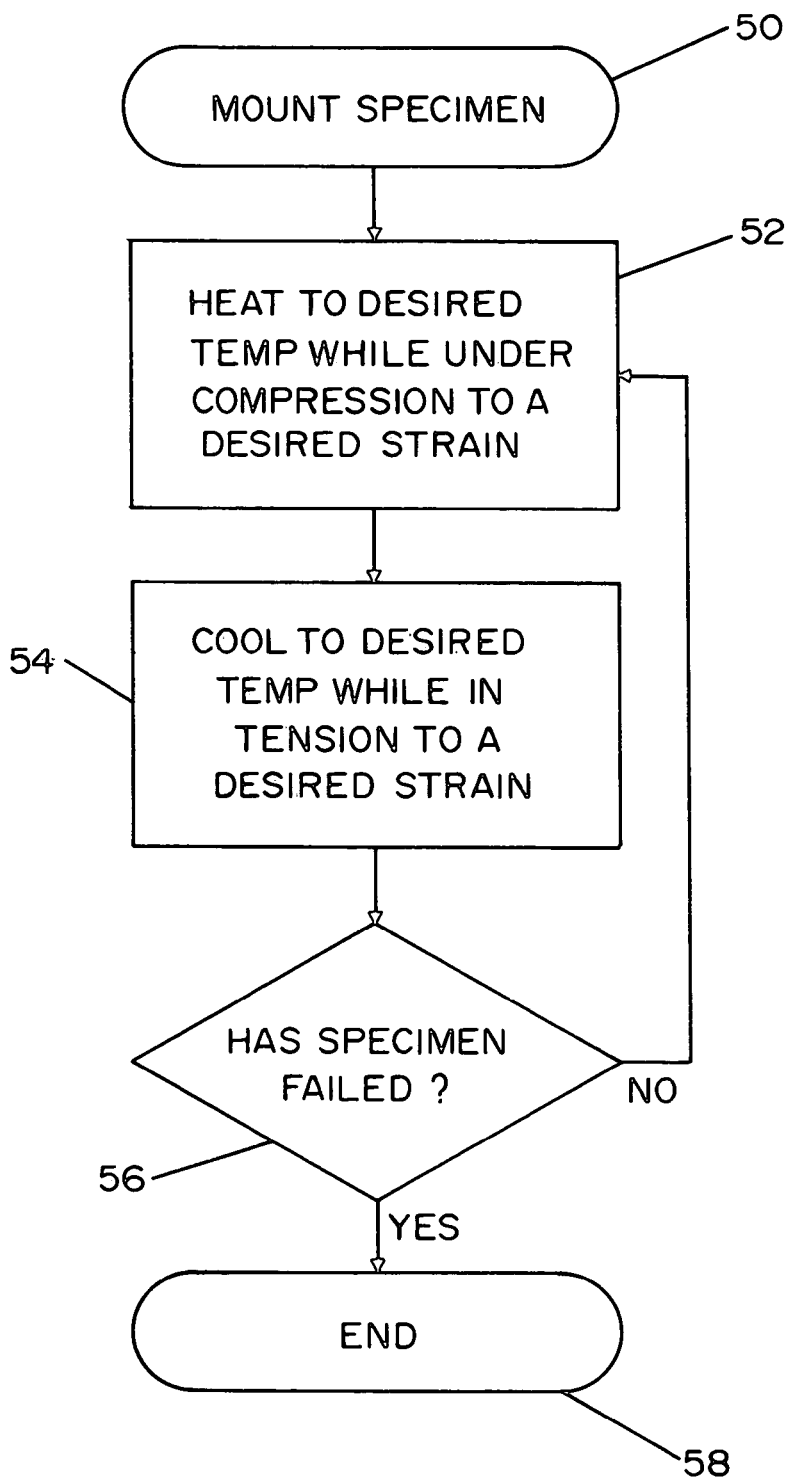
FIG. 5 is a flow diagram of a method for evaluating thermal fatigue resistance of a welding consumable alloy.

FIG. 5 depicts a general procedure for performing the test method. With reference to FIG. 5, the specimen 18 (FIGS. 6 and 7) is mounted in the testing machine 20 (FIG. 7) at step 50. The test specimen 18 is then heated to a desired temperature while under compression, which is shown at step 52. The test specimen is then cooled to a desired temperature while in tension, which is shown at step 54. If the test specimen has not failed, e.g. the specimen has not broken, then the test specimen is heated to the desired temperature while under compression. The decision as to whether the test specimen has failed is depicted at step 56. As seen in FIG. 5, steps 52 and 54, i.e. heating under compression and cooling in tension, are repeated until the specimen fails. Once the specimen fails the test method is complete, which is depicted at 58.

A specific example of a test method that has been performed on a particular alloy will be described to teach one skilled in the art how to perform the test method. The inventive method is not limited to the values described in the specific example. Instead, the inventive method includes the broad concepts that encompass the specific disclosure.

Figure 8:
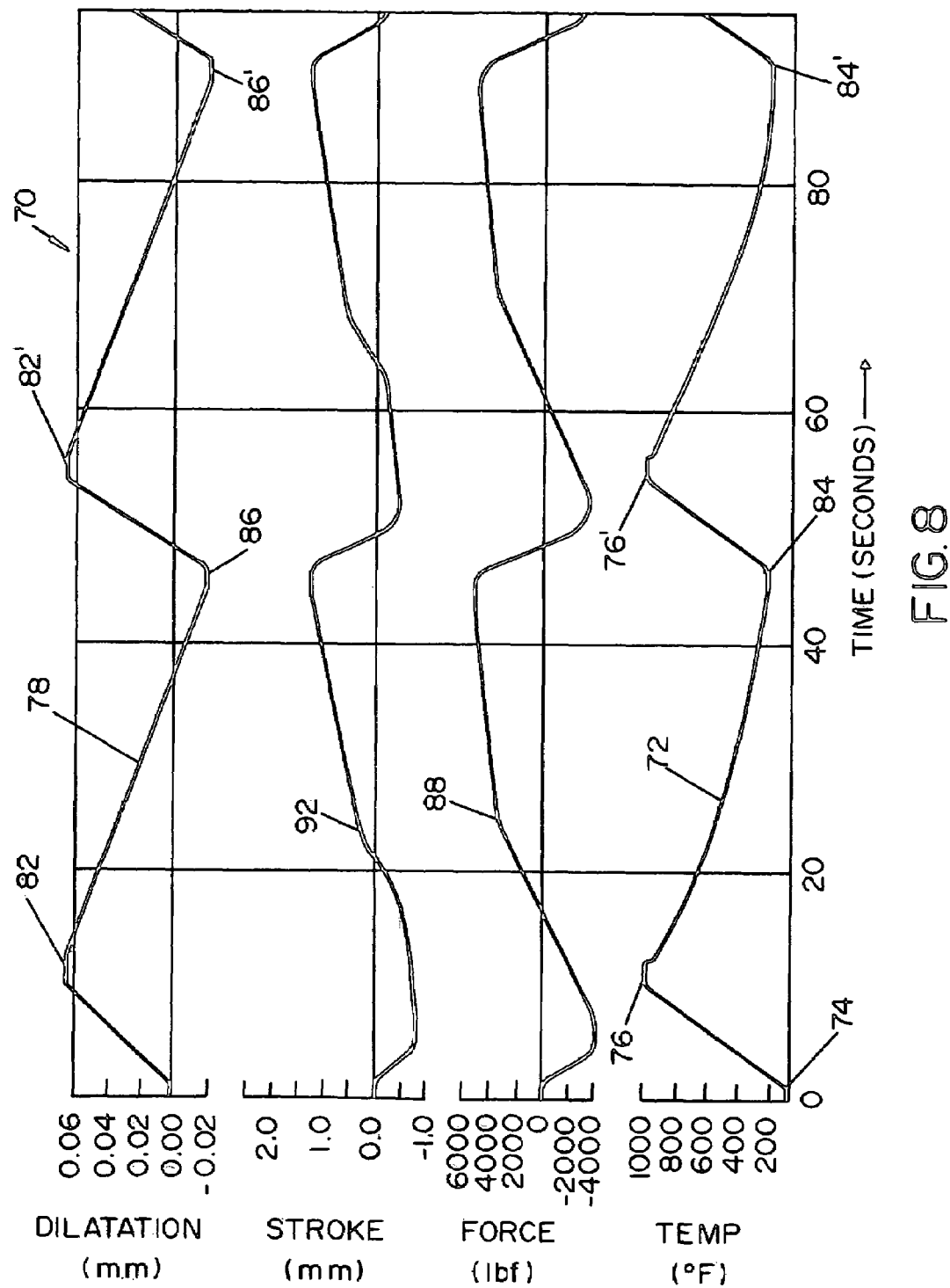
FIG. 8 is a graph of temperature, force, stroke and dilatation, each as a function of time for two cycles of a test method for evaluating thermal fatigue resistance for a welding consumable alloy.
Figure 9A:
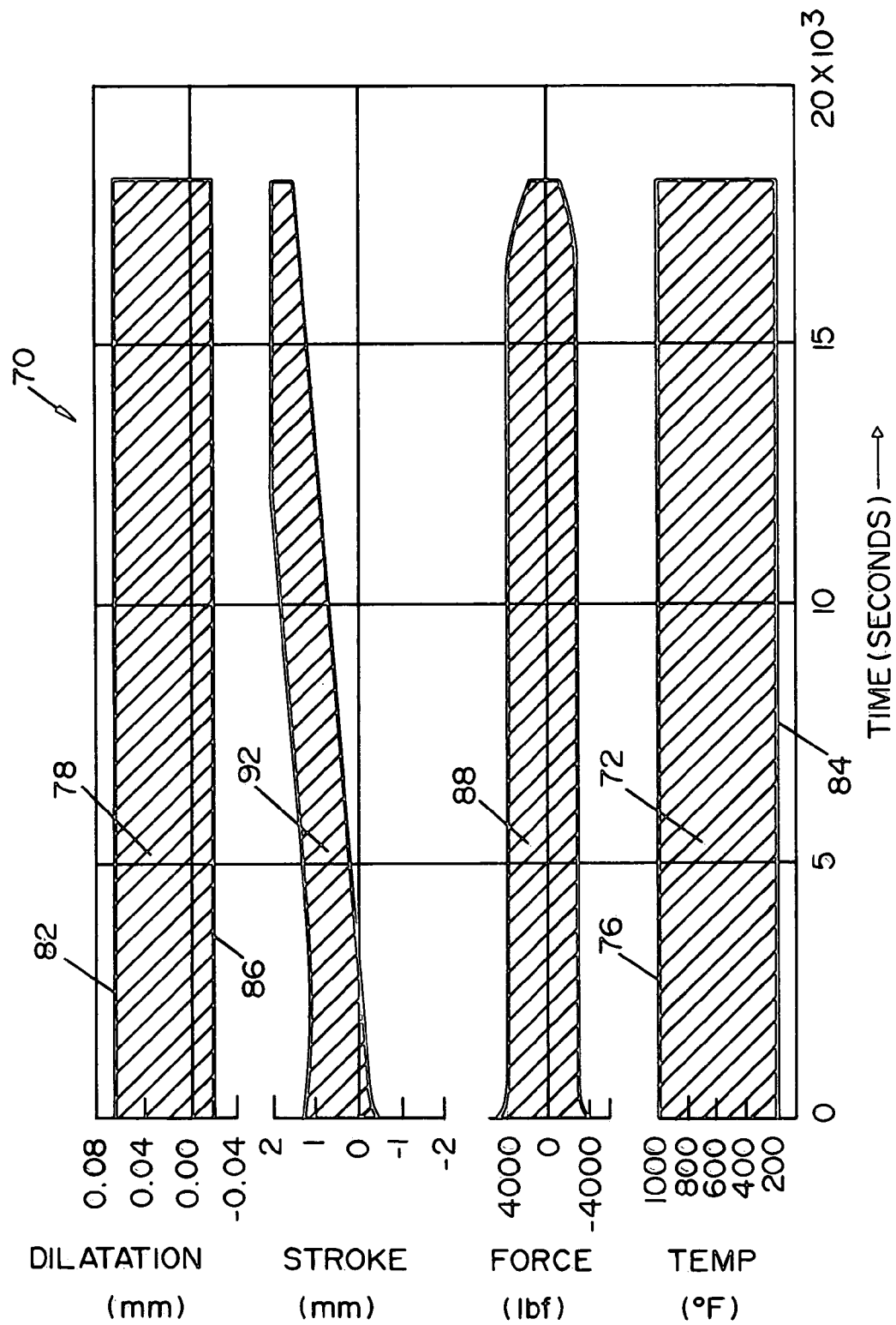
FIGS. 9A and 9B are graphical depictions of temperature, force, stroke and dilatation, each as a function of time up to failure of two different alloy specimens in the method for evaluating thermal fatigue resistance for a hardfacing welding consumable alloy.

Description of the test method that has been performed will be made with reference to the graphs depicted in FIGS. 8, 9A and 9B. FIG. 8 depicts a graph 70 that plots (1) dilatation, i.e. the change in diameter of the specimen, as a function of time, (2) jaw stroke as a function of time, (3) force exerted on the specimen as a function of time and (4) temperature of the specimen as a function of time. The graph 70 of FIG. 8 only shows the first and second cycles of the test method. This is done for clarity. After properly placing the sample specimen 18 into the testing machine 20, the sample specimen was heated, as depicted by plot 72 in FIG. 8, from a first temperature (room temperature), as depicted at 74 to a second temperature (1000° F.), as depicted at 76 at a first rate (100° F./s). The rate of heating can be determined by the slope of plot 72 between point 74 and point 76. Heat was introduced to the specimen 18 via electrical resistance heating. As seen in FIG. 8, while being heated the test specimen underwent a gradual compressive strain, depicted at plot 78, up to a maximum compressive dilatation $\Delta d_{comp}^{max}$, depicted at 82. Dilatation was measured at the diameter of the specimen. In the performed method $\Delta d_{comp}^{max}$ equaled 0.06491 mm. Since the initial diameter of the test specimen was 6.35 mm, the compressive strain at 10000° F. ($\epsilon_{1000}$) measured 0.010, where $\epsilon=\Delta d/d (0.010=0.06491 \text{ mm}/6.35 \text{ mm})$.

After reaching the second temperature (1000° F.) 76 and the maximum compressive dilatation 82, the sample specimen 18 was then free cooled, i.e. without a controlled cooling rate, from the second temperature (1000° F.) 76 to a third temperature (200° F.), depicted at 84. The specimen was free cooled by no longer introducing an electrical current to the specimen. Even though the cooling was uncontrolled for the specimens tested using the described method, the average cooling rate was between 20° to 22° F./s, as seen by the slope of plot 72 between points 76 and 84. During the cooling step argon gas was introduced to the region surrounding the sample specimen 18. While being cooled, the test specimen underwent a gradual tensile strain to a maximum tensile dilatation $\Delta d_{tensile}^{max}$, depicted at 86 of −0.02 mm measured at the diameter of the sample specimen. Accordingly, the tensile strain at 200° F. ($\epsilon_{200}$) measured −0.003, where $\epsilon=\Delta d/d$ (−0.003=−0.02 mm/6.35 mm).

After reaching the maximum tensile dilatation, depicted at 86, and the third temperature, depicted at 84, the sample specimen 18 was then heated again from the third temperature (200° F.) to the second temperature (1000° F.), depicted at 76' at the first rate (100° F./s), while the specimen underwent the gradual compressive strain up to the maximum compressive dilatation $\Delta d_{comp}^{max}$, depicted at 82' (0.06491 mm). Subsequently, the sample specimen was free cooled from the second temperature (1000° F.) 76' to the third temperature (200° F.), depicted at 84' while the specimen underwent the gradual tensile strain up to the maximum tensile dilatation $\Delta d_{tensile}^{max}$, depicted at 86' (−0.02 mm).

So that the specimen 18 underwent the desired dilatation, a force was applied to the specimen. The plot of this force is depicted at 88. To apply the desired force, at least one of the jaws 22 (FIG. 7) of the testing machine 20 (FIG. 7) were moved and the stroke of one of the jaws, i.e. the distance the jaw moved from its original position, was plotted at 92. The heating and cooling between the second temperature and the third temperature, along with the loading that results in the desired dilatation, which corresponds to a desired strain, was repeated until the sample specimen failed.

The strain, which is a function of the dilatation, and the temperature are controlled input for the depicted test method. FIG. 9A depicts the graph 70 of FIG. 8 plotting the dilatation, the stroke, the force and the temperature each as a function of time until failure of the specimen 18. Since the entire test has been plotted in FIG. 9A, for the purposes of clarity FIG. 9A only depicts the maximum and minimum value for each measured value, i.e. dilatation, stroke; force and temperature versus time. Between the maximum and minimum values for each measured value, the plot at graph 70 in FIG. 9A would look similar to the plot at graph 70 in FIG. 8. As can be seen in FIG. 9A, the maximum compressive dilatation 82 and at the maximum tensile dilatation 86 remain constant, or at least substantially constant, throughout the test method until failure of the specimen. Likewise, the specimen is heated and cooled between the second temperature 1000° F., depicted at 76, and the third temperature 200° F., depicted at 84, throughout the test method until failure of the test specimen. The stroke of the moving jaw 22 of the testing machine 20 and the force applied on the test specimen 18 varied to maintain the desired maximum compressive and tensile strains in each cycle. Accordingly, as seen in FIG. 9A, the stroke of one of the jaws 22 (FIG. 7) will decrease and the force on the sample specimen will also decrease as the number of cycles increase until failure of the specimen.

Figure 9B:
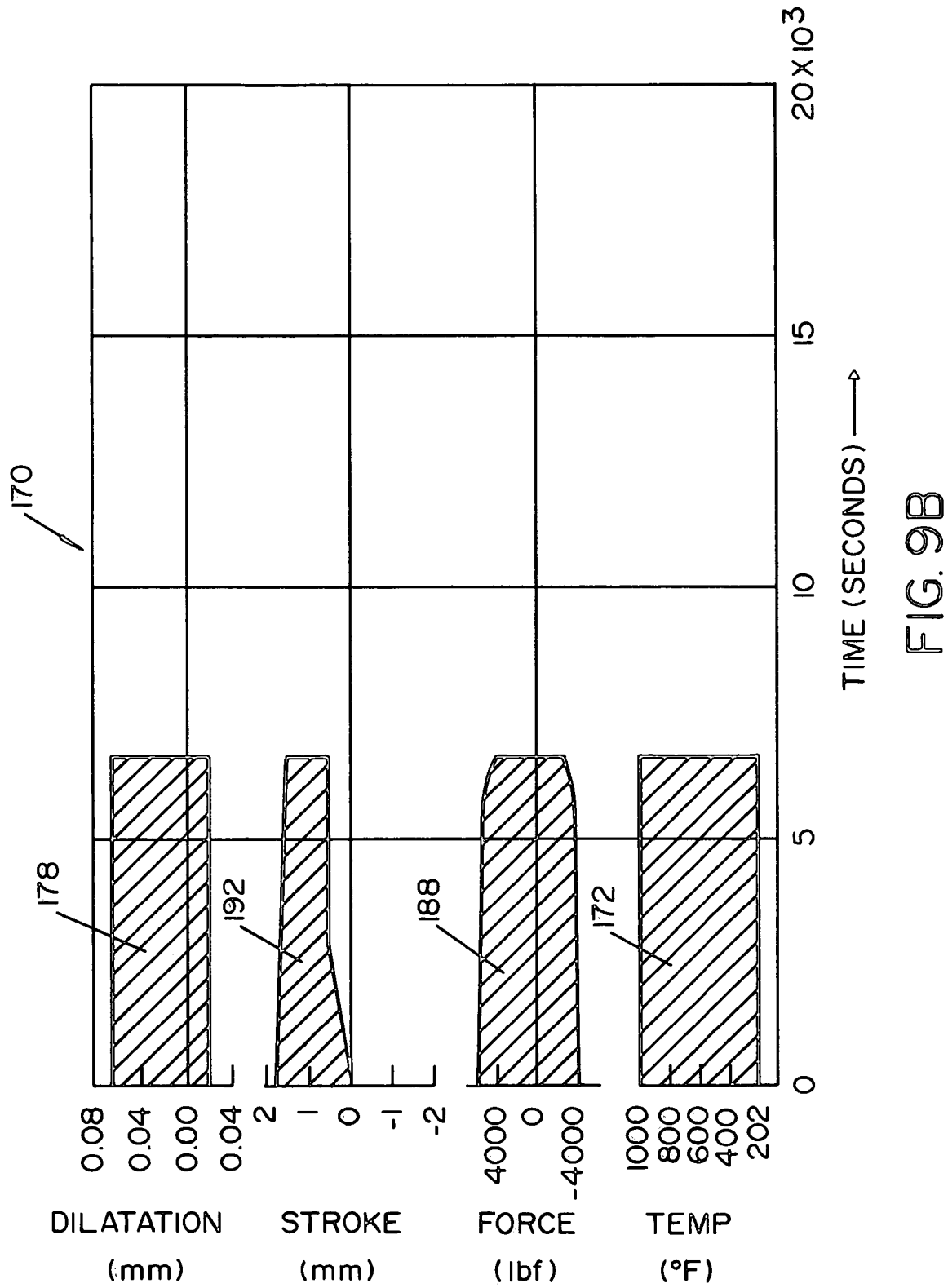

FIG. 9B depicts a graph 170 that is for a test specimen made from a different alloy. The graph 170 is similar to the graph 70 of FIG. 9A in that dilatation, stroke, force and temperature are graphed, each as a function of time. Again, since the entire test is depicted, i.e. until failure of the specimen, only the maximum and minimum values are depicted. As seen in graph 170, the maximum compressive dilatation and the maximum tensile dilatation each remain constant, or substantially constant, as shown at plot 178. Likewise, the specimen is heated and cooled between two desired temperatures seen at plot 172, after the specimen has been brought up from room temperature, throughout the test method until failure of the specimen. Also, the stroke of the jaws varied as the specimen neared failure, as seen at plot 192. The force on the specimen also varied as the specimen neared failure, as seen at plot 188.

The preprogrammed dilatations were chosen as a function of the inherent strength of the alloy that was tested to introduce a small amount of compressive plastic strain during heating and a small amount of tensile plastic strain during cooling. Accordingly, the test specimen underwent a small amount of permanent deformation during each cycle.

The mechanical strain on the test specimen was also calculated. The mechanical strain $\epsilon_{mech}$ is the strain on the test specimen due to the stress imposed on the specimen, not taking into account any thermal effects. Accordingly, the total strain $\epsilon_{total}$ equals the mechanical strain $\epsilon_{mech}$ added to the thermal strain $\epsilon_{thermal}$ ($\epsilon_{total}=\epsilon_{mech}+\epsilon_{thermal}$). To determine the mechanical strain that the specimen underwent, both compressive and tensile, the following calculations were performed.

For the method described above, assuming pure thermal expansion of the sample specimen and that the sample specimen has thermal properties similar to ferrite, the change in diameter of the sample at 200° F. and 1000° F. due to thermal expansion can be calculated by the following formula $\Delta d_{thermal}=d_0\{\alpha_{Ferrite}[T_2-T_1]\}$. Where the thermal expansion coefficient of ferrite ($\alpha_{Ferrite}$), assuming the alloy to have similar thermal properties, is 1.4×10-5 (mm/mm)/° C. and the initial diameter ($d_0$) of the sample is 6.35 mm, the expected dilation at 200° F. $\Delta d_{thermal}^{200}$ equals 0.0062 mm and the expected dilation at 1000° F. $\Delta d_{thermal}^{1000}$ equals 0.0457 mm. Assuming an isothermal temperature in the test specimen, the mechanical compressive strain and the mechanical tensile strain can be computed knowing the dilatation due to thermal stresses.

Referring back to FIG. 8, during the test method, at 200° F. the total change in diameter $\Delta d_{total}^{200}$ was −0.02 mm. During the test method at 1000° F. the total change in diameter $\Delta d^{total1000}$ was 0.06491 mm. Since, $\Delta d_{total}=\Delta d_{thermal}+\Delta d_{mechanical}$, then $\Delta d_{mechanical}^{200}=-0.0262$ mm, which is −0.02 mm −0.0062 mm, and $\Delta d_{mechanical}^{1000}=0.0192$ mm, which is 0.06491 mm −0.0457 mm.

To determine the mechanical strain at a particular temperature, the changes in diameter due to the thermal effects on the sample specimen are taken into account. The diameter of the sample specimen at a particular temperature ($d^{temp}$), which for the described method was 200° F. and 1000° F., was found using the formula $d^{temp}=d_0+\Delta d_{thermal}$. As found above, $\Delta d_{thermal}^{200}$ equals 0.0062 mm so that $d^{200}=6.3562$ mm, which is 6.35 mm+0.0062 mm. Also as found above, $\Delta d_{thermal}^{1000}$ equals 0.0457 mm so that $d^{1000}=6.3957$, which is 6.35 mm+0.0457 mm.

The strain of a specimen can be found using the formula $\epsilon=\ln(1+(\Delta d/d_0))$. To determine the mechanical strain, for the preceding formula $d_0$ will be equal to $d^{200}$ for the mechanical strain at 200° F. and to $d^{1000}$ for the mechanical strain at 1000° F. Also to determine the mechanical strain, $\Delta d$ will equal the change in diameter only due to mechanical strain, which is $\Delta d_{mechanical}^{200}$, which is −0.0262 mm at 200° F. and $\Delta d_{mechanical}^{1000}$, which is 0.0192 mm at 1000° F. According to the strain formula above, the true tensile strain at 200° F. equals −0.004, which is $\ln(1+(-0.0262/6.3562))$, and the true compressive strain at 1000° F. equals 0.003, which is $\ln(1+(0.0192/6.3975))$. As can be seen from the above calculations, a small mechanical compressive strain and a small mechanical tensile strain was applied to the test specimen during each cycle.

A test method for evaluating thermal fatigue resistance of an alloy has been described with reference to a specifically described method that has been performed. Modifications can be made to the method, and the invention includes such modifications that come within the scope of the appended claims or the equivalents thereof.

The invention claimed is:

1. A method for evaluating thermal fatigue resistance for a welding consumable alloy, the method comprising:
   placing a test specimen of a welding consumable alloy in a testing device such that a tensile load and a compressive load can be introduced to the test specimen;
   heating the test specimen to a first temperature;
   applying a compressive force to the test specimen while heating the test specimen to the first temperature;
   cooling the test specimen to a second temperature;
   applying a tensile force to the test specimen while cooling the test specimen to the second temperature; and
   repeating the heating step, the applying a compressive force step, the cooling step and the applying a tensile force step until the test specimen fails, wherein at least one of the applying a compressive force step and the applying a tensile force step is repeated varying the force that is applied on the test specimen so that the test specimen deforms about the same percentage of its original diameter during an at least substantial portion of the method.

2. The method of claim 1, wherein the applying a compressive force step comprises applying a great enough compressive force to the test specimen such that the test specimen permanently deforms.

3. The method of claim 2, wherein the applying a tensile force step comprises applying a great enough tensile force to the test specimen such that the test specimen permanently deforms.

4. The method of claim 1, wherein the heating step comprises heating the test specimen at a substantially constant rate.

5. The method of claim 4, wherein the first temperature equals about 1000° F.

6. The method of claim 5, wherein the substantially constant rate equals about 100° F./s.

7. The method of claim 4, wherein the cooling step comprises free cooling the test specimen.

8. The method of claim 4, wherein the second temperature equals about 200° F.

* * * * *